United States Patent [19]

Baughman et al.

[11] Patent Number: 5,102,805
[45] Date of Patent: Apr. 7, 1992

[54] METHOD FOR DETECTING THE PRESENCE AND CONCENTRATION OF WEAK ACIDS AND BASES IN LIQUIDS

[75] Inventors: Ernest H. Baughman, Naperville, Ill.; Karl G. Schick, Milwaukee, Wis.; Barbara R. Coughlin, Seattle, Wash.

[73] Assignee: Amoco Corporation, Chicago, Ill.

[21] Appl. No.: 438,339

[22] Filed: Nov. 16, 1989

[51] Int. Cl.⁵ .................. G01N 33/00; C01B 17/16
[52] U.S. Cl. .................. 436/113; 423/228; 423/229; 472/80; 472/81
[58] Field of Search .......... 436/121, 126, 133, 134, 436/136, 174, 175, 177; 422/80, 81, 82; 423/228, 229

[56] References Cited

U.S. PATENT DOCUMENTS

| | | | |
|---|---|---|---|
| 3,607,073 | 7/1968 | Stamm | 436/140 |
| 3,773,469 | 11/1973 | Hiser et al. | 422/68.1 |
| 4,740,473 | 4/1988 | Tomlin | 436/52 |
| 4,798,910 | 1/1989 | Herrin | 423/228 |
| 4,818,348 | 4/1989 | Stelter | 436/52 |

FOREIGN PATENT DOCUMENTS 231741 9/1982 Japan.
107495 5/1984 Japan.

Primary Examiner—David L. Lacey
Assistant Examiner—Thomas E. Daley
Attorney, Agent, or Firm—Ekkehard Schoettle; William H. Magidson; Ralph C. Medhurst

[57] ABSTRACT

The concentration of weak acid and weak base constituents, or their soluble salts, in liquids is determined by passing succeeding samples of constant volume to a separation zone wherein target constituents are volatilized by reagents, then volatilized analytes are stripped from the liquid matrix and carried to a detection zone at a constant flow rate, wherein signals proportional to the variations in individual target analyte concentrations between succeeding samples are generated.

31 Claims, 6 Drawing Sheets

METHOD FOR DETECTING THE PRESENCE AND CONCENTRATION OF WEAK ACIDS AND BASES IN LIQUIDS

BACKGROUND OF THE INVENTION

This invention relates to novel apparatus and methods useful for determining the concentration of weak acid or weak base components, or their soluble salts, in liquids containing such acid, base or salt.

It is well known that it is useful to be able to determine the concentration of weak acid and base constituents, or their soluble salts, in liquids for the purpose of monitoring and controlling processes. Weak acids are characterized as being partially ionized in water solutions (i.e., $H_2S$, $CO_2$, $HCN$ and $CH_3CO_2H$), in contrast to strong acids which are fully ionized in water (i.e., $H_2SO_4$). Weak bases (i.e., $NH_4OH$) can be similarly distinguished from strong bases (i.e., $NaOH$). Salts are produced by the reaction between acids and bases. Soluble salts are capable of mixing with liquids to form solutions. For example, the reaction between $H_2S$, an acid, and monoethanolamine, a base, produces monoethanolamine bisulfide, a soluble salt. Unless otherwise indicated, any reference to detecting weak acid and base components in this application should be deemed to encompass detection of the soluble salts of such weak acid or base, if any. Determination of the concentration of weak acid and base constituents, or their soluble salts, in liquids is useful in, but in no way limited to, amine system control and waste water treatment. Of particular importance is the continuous on-line measurement of the quality of industrial process streams containing weak acid and base components, or their soluble salts.

Amine system control methods based on the measurement of $H_2S$ in rich amine are taught, for example, in U.S. Pat. Nos. 3,958,943 and 4,289,738 which are hereby incorporated by reference and made a part hereof. Typically, liquid amine is used to remove acid impurities, such as hydrogen sulfide and carbon dioxide, from gas. The amine is contacted with the gas so as to cause the impurities to be absorbed by the amine. Then the amine is regenerated by stripping acid gases out, leaving a lean amine that is suitable for recontacting with gas. Stripping is accomplished by heat input or pressure decrease. The degree to which acid gases are stripped from rich amine depends on the amount of heat used or the pressure drop. Over-stripping, or removing more acid gas than necessary to regenerate amine, results in an energy penalty. On the other hand, government regulations limit the maximum amount of of $SO_2$ that may be generated when gas is combusted. Since $SO_2$ is generated when $H_2S$ is burned, understripping (removing too little acid gas) can result in environmental penalities or unsalable gas.

An optimum amount of acid gas should be removed from amine to avoid understripping yet minimize energy costs. Prior art teaches that amine system heat input should be based on the amount of hydrogen sulfide absorbed by the amine: the greater the amount of acid gas absorbed, the more heat input required to liberate the acid gas from the amine. Clearly, the importance of determining the concentration of weak acids in liquids is well known.

Increasingly strict environmental regulations have made it vital to prevent prohibited discharges from waste systems. To this end, the usefulness of monitoring waste water for $NH_3$ content is well known. When $NH_3$ content exceeds acceptable levels, the water can be diverted to buffer storage away from waste treatment systems thereby avoiding upset of the treatment process. In addition, neutralization of foul water by the addition of treating chemicals can be optimized using control based on the monitoring of weak base constituents dissolved in the water.

A review of the art reveals that limited means are presently available to achieve the desired determinations. Hydrogen sulfide detection may be attempted using several commercially available analyzers. However, no commercially available instrument is capable of essentially continuous on-line analysis of hydrogen sulfide and carbon dioxide. Further disadvantages of present analysis apparatus include: uncorrected drift, inability to distinguish interfering components from analytes and analyzer response that is adversely affected by pH, color, turbidity and temperature. As a result, commercially available hydrogen sulfide analyzers lack the degree of accuracy and repeatability necessary for continuous on-line measurement.

A method for determining the concentration of a carbonate and a sulfite in a liquid is disclosed in U.S. Pat. No. 4,663,724. A commercial device employing the teachings of the '724 patent is not available. The method involves calculating the concentrations of $CO_2$ and $SO_2$ in a liquid based on the concentrations of $CO_2$ and $SO_2$ determined for a continuously flowing sample stream, the flow rate of the sample stream and the flow rate of a carrier gas. It remains to be seen whether the '724 disclosure is practical since it relies on calculations which are very sensitive to flow measurement inaccuracies.

As previously mentioned, for amine system control it is useful to know not only $H_2S$ content of amine, but also $CO_2$ content. While the reasons for this are described below in detail, at this point it is sufficient to say that, in general, $H_2S$ represents only a fraction of the total acid gas present in lean amine. Therefore, total acid gas is a better measure of lean amine quality so that $H_2S$ and $CO_2$ content should both be used to control regenerator heat input. Not only is instrumentation presently unavailable to make these determinations, but there is a general lack of appreciation in the art for the importance of measuring total acid gas content in amine streams used to remove impurities from gas.

The shortcomings of the art present those in processing industries with a dilemma. The usefulness and desirability of having detection apparatus and methods for continuous determination of the concentration of weak acid and base constituents dissolved in liquids is recognized, yet suitable devices and methods have not been developed to achieve this type of on-line analysis. As a result, it is customary in amine system control, for example, to obtain samples for analysis once per shift. The time lag between obtaining samples, transporting them to central laboratory facilities and performing analyses frustrates the effective utilization of analysis results in process control. By the time process operations are modified based on this sample analysis, conditions have already changed. While such time lag in obtaining analysis results impairs continuous feedback process control, it is fatal to most continuous feed-forward process controls. This is because feed-forward systems adjust downstream operating conditions in response to variations in upstream influent quality. The determination of influent quality must be on-line and continuous in such a system.

Similarly, typical waste treating control involves capturing samples for analysis in a laboratory. Water treating chemical addition rates may be based on analysis performed as infrequently as once per month. The time lag between sampling and process control using analysis results impairs effective upset prevention and causes uneconomical treatment of waste water.

SUMMARY OF THE INVENTION

The present invention overcomes the problems and disadvantages of the prior art by providing a method and apparatus for on line determination of the concentration of weak acid or weak base components of one or more liquid streams. Substantially all of the acid or base components of each of a plurality of individual, succeeding liquid samples of essentially constant size are volatillized by contact with a reagent in a separation zone. The volatilized analytes are stripped from the liquid matrix within the separation zone by means of an analyte carrier stream which flows at a substantially constant rate. Volatilized analytes are transported to a detection zone by the analyte carrier stream. The concentration of volatilized analytes is determined in the detection zone and a control signal proportional to analyte concentration is generated. These signals may be used for a variety of quality analysis and process control functions.

Samples are introduced into the separation zone by means of a sample carrier stream which flows from a sample port to the separation zone. The continuously flowing sample carrier one sample away from the sample port before succeeding samples enter the stream. Liquid or gas phase sample carrier fluids may be employed. Sample carrier fluids may react chemically with sample components unless such reaction interferes with the smooth flow of sample carrier. Where separation reagent is used as sample carrier fluid, the sample carrier steam itself is part of the separation zone. Where an inert sample carrier fluid is used (i.e., a fluid which does not substantially chemically react with target constituents), the sample carrier stream is not part of the separation zone.

Reagent may be introduced into the separation zone as sample carrier fluid or through a separate reagent inlet into the separation zone. In the case of target acid constituents (including soluble salts of acids), volatilization is achieved using a strong acid reagent such as 10 N sulfuric acid. When base constituents or their soluble salts are targeted, a strong base reagent, such as 10 N sodium hydroxide, is used. Volatilization may occur as a result of a reaction between target constituents and reagents (i.e., bisulfides in a sample will react with sulfuric acid to form $H_2S$), or through a dissociation process where the resulting volatilized analyte is the same species as the target constituent (i.e., carbon dioxide dissolved in an amine solution).

Volatilized analytes may be entrained in liquids within the separation zone, although it is likely that a portion of the volatilized analytes will spontaneously migrate from the liquid to a vapor space within the separation zone. Entrained volatilized analyte is separated from the liquid by means of upwardly flowing gas bubbles. The gas flows into the separation zone from an analyte carrier stream inlet which is located below the liquid level inside the separation zone. Generally, analyte carrier gas is inert (i.e., does not substantially chemically react with the other contents of the separation zone), however, analyte carrier gas may be selected so as to react chemically with volatilized analytes resulting in a more readily detectable analyte species. The separation zone is configured so that any volatilized analyte separated from the liquid is carried by the analyte carrier gas from the separation zone to the detection zone through a vapor outlet.

A variety of detection devices may be used to determine the amount of analyte released from the sample matrix. For example, gas phase detection of $CO_2$ and $h_2S$ can be achieved using spectrophotometric detectors. The Model No. IR-703 infrared analyzer, manufactured by Infrared Industries, Inc., of Santa Barbara, Calif., is one such device which is capable of gas phase measurement of $CO_2$. The Model No. 400 Photometric Analyzer, manufactured by the E. I. du Pont de Nemours & Co., of Wilmington, Del., is one such device which is capable of gas phase measurement of $H_2S$. Liquid phase detection $NH_3$ can be achieved using conductivity detectors. Gaseous $NH_3$ removed from the sample matrix is allowed to diffuse in a liquid stream using, for example, a PN 85-705 diffusion cell, manufactured by FIAtron Process Systems, Inc. (FIAtron) of Oconomowoc, Wis. The FIA-Duct 500 Conductivity Detector, also manufactured by FIAtron, is but one commercially available instrument which is capable of liquid phase measurement of $NH_3$.

It is critical that the following conditions be met in order for the method and apparatus described herein to perform properly:

1. the amount of unreacted reagent in the separation zone must be maintained at a concentration sufficient to cause substantially complete volatilization of analytes each time succeeding samples are introduced into the separation zone; and 2. each succeeding sample must be of essentially constant volume; and 3. the rate at which analyte carrier gas passes through the separation zone to the detection zone must be essentially constant.

Also important, but not as critical (acceptable approximate tolerances are indicated in parentheses), the following conditions enhance the effectiveness, accuracy and repeatability of the invention:

1. succeeding samples, as well as the separation zone itself, should remain at a relatively constant temperature (i.e., ±20° F.);

2. succeeding samples should be introduced into the sample carrier stream at relatively constant time intervals (i.e., within ±25% of set point);

3. the flow rate of the sample carrier stream should be relatively constant (i.e., within ±10% of set point);

4. the flow rate of reagent into the separation zone through the reagent stream inlet should be relatively constant (i.e., within ±10% of set point); and 5. the volume of liquids within the separation zone should be relatively constant (i.e., within +5% of set point). While some variation is tolerable, in the practice of the invention it is rare that there is much deviation in the volume of liquids in the separation zone. This is primarily due to the configuration of the separation zone, as described in greater detail below.

By meeting all of these conditions, it is possible to substantially limit the number of system variables to one: the concentration of target constituents in the liquid stream from which samples are taken. Those skilled in the art of process analytical instrumentation will understand that it may be possible to alter one condition if an appropriate countermeasure is taken. However, the preferred embodiment of the method described herein incorporates the above conditions thereby achieving the most economically improved practice of the invention.

The pulsed nature of the concentration determinations is exploited for monitoring potential detection instrument drift. For instance, spectrophotometric detectors can be calibrated to a baseline reading when only analyte carrier gas is present. As volatilized analytes pass through the detectors, "peaks" occur which represent the amount of radiation absorbed by the analytes. Between peaks, absorbance measurements should return to the baseline reading. "Peak" output from the detector can be used to determine analyte concentration while "baseline" output occurring between peaks can be used to verify that the detector drift has not occurred. Depending on the degree of accuracy desired, instrument maintenance alarms can be triggered when baseline drift exceeds allowable limits.

Improved amine system control can be achieved by inputting only as much steam into an amine regenerator as is required to achieve desired leanness. Control of steam input is based on continuous determination of acid gas content of amine, both before and after regeneration, using, for example, analysis methods and apparatus disclosed herein.

Water treatment improvements can be achieved, for example, by using analysis methods and apparatus disclosed herein to continuously monitor ammonia levels in waste water. For instance, various water treatment methods employ microorganisms to digest organic waste. The microorganisms require nitrogen and other nutrients to grow. Ammonia in water treatment system influent represents a source of nitrogen, although excess ammonia (i.e., levels above microorganism nutritional requirements) will pass through the system, sometimes causing permit levels to be exceeded. Such excursions can be prevented by diverting waste water with excess ammonia to buffer storage, then feeding it into the treatment system when influent conditions change. It is important, therefore, that ammonia in influent be monitored so that microorganism nutritional requirements can be satisfied and, at the same time, so that permitted ammonia levels for the discharge of treated water can be met. In addition, pretreatment of waste water (i.e., pH control) would cost less, both in terms of equipment and chemicals consumed, if performed on a continuous basis using automatic control rather than by batch as is typical at present. Continuous control requires continuous on-line determination of acid or base in water.

The accompanying drawings, which are incorporated in and constitute a part of this specification, illustrate one embodiment of the invention, and together with the description serve to explain the principles of the invention.

DETAILED DESCRIPTION OF THE INVENTION

Figure 1:
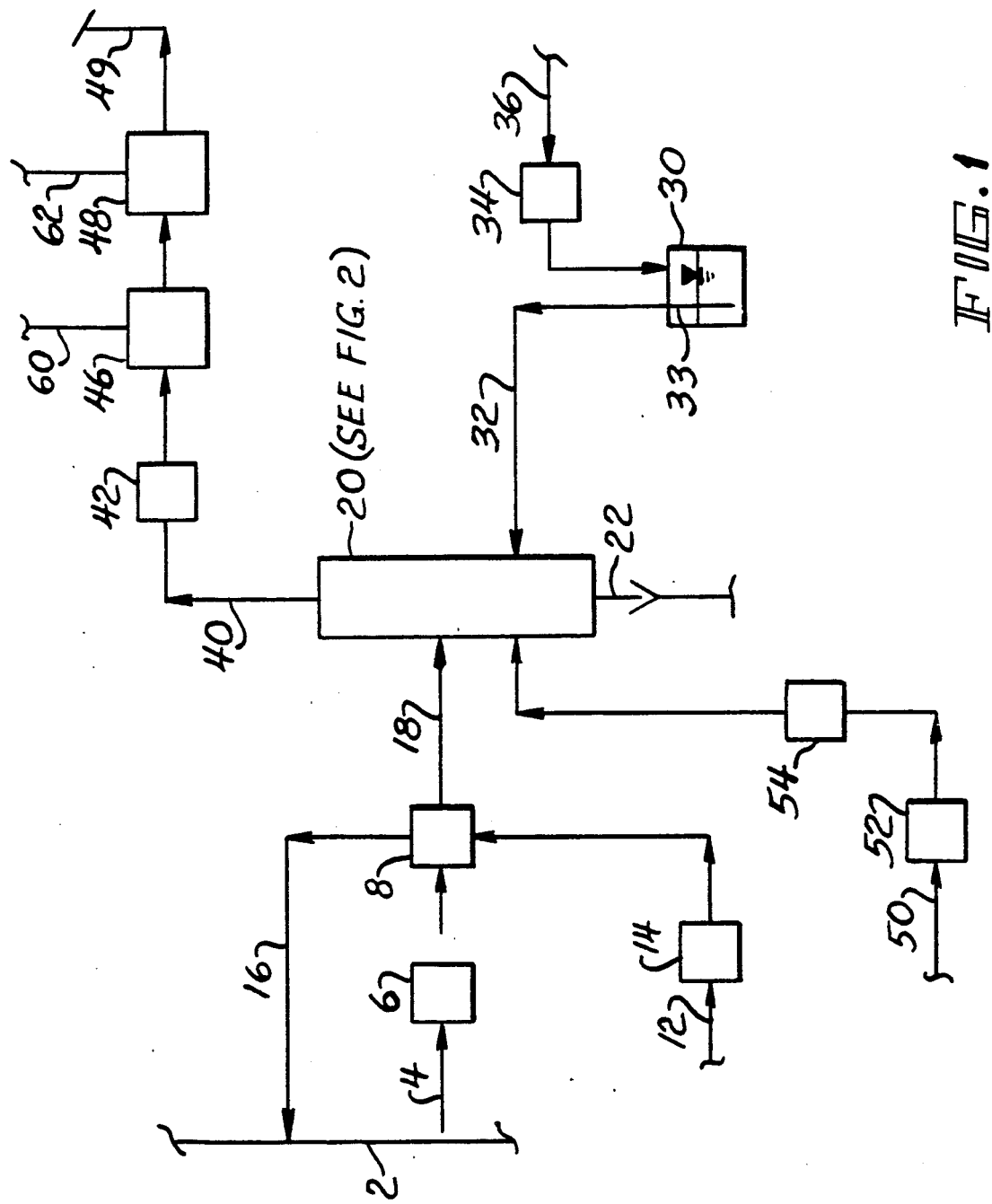
FIG. 1 is a diagram showing an improved apparatus and method for determining the concentration of weak acid and base constituents dissolved in liquids.

Referring to FIG. 1 of the drawings, there is shown a system which can be used for carrying out a method embodying this invention. A sample stream 4 leads from liquid stream 2 through sample flow indicator 6 to sample port 8. At the same time, carrier fluid stream 12 flows from a source not shown at a flow rate indicated and controlled by carrier fluid flow indicator and controller 14 to sample port 8. Sample port 8, preferably a six port valve, such as the commercially available Model No. 3527330 manufactured by Combustion Engineering of Lewisburg, W. Va., is effective to capture samples of constant size from sample stream 4 and deliver these samples into carrier fluid stream 12 which, upon exiting from sample port 8, flows through sample carrier stream 18 into separator vessel 20. It is critical that the samples of the process liquid be of essentially the same size. Liquids delivered to sample port 8, but not used for sampling, is returned to liquid stream 2 through sample return stream 16. In this manner, the liquid flowing through sample stream 4 is maintained to be representative of the liquid flowing at essentially the same time through liquid stream 2.

Figure 2:
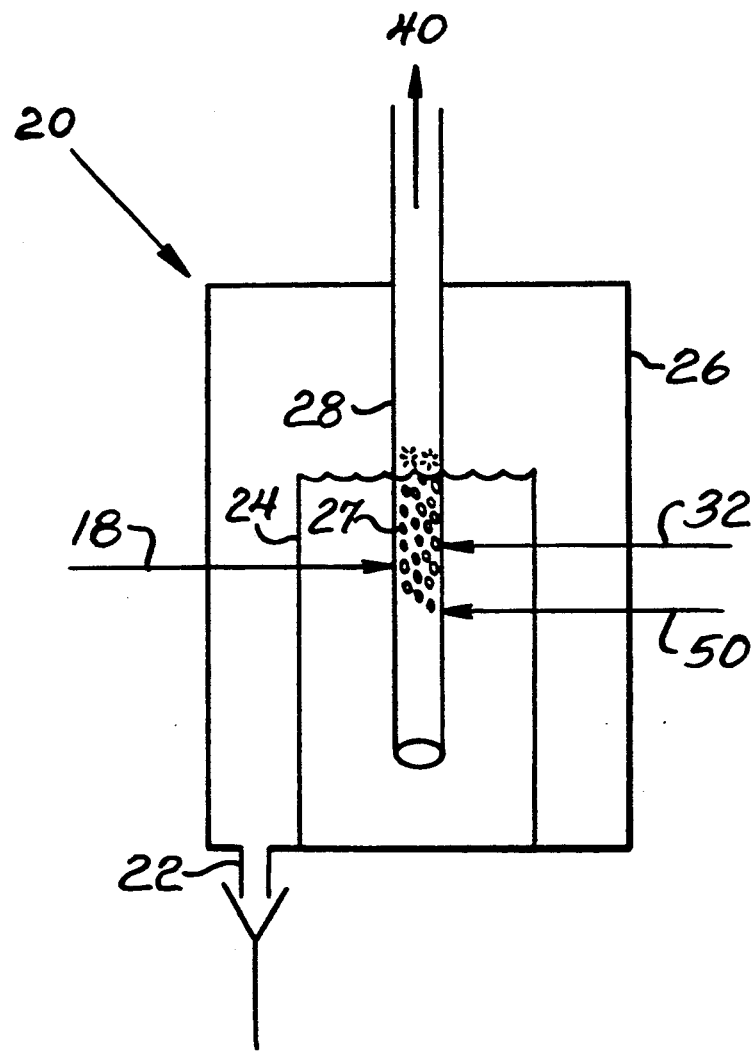
FIG. 2 is a cross-sectional schematic view of the internal elements of a separation chamber that is a part of the apparatus and method set forth in FIG. 1.

Referring to FIG. 2, the configuration of separator vessel 20 can be seen in greater detail. Separator vessel shell 26 is an enclosure which is airtight with inlets for sample carrier stream 18, reagent inlet stream 32, described in more detail below, and analyte carrier stream 50, also described in more detail below, and outlets for separator vessel drain 22 and separator vessel vapor outlet stream 40 described in more detail below. Liquids container 24 is positioned inside separator vessel shell 26. During normal operation, liquid flows into liquid container 24 through sample carrier stream 18 and reagent inlet stream 32. Liquid overflowing the liquid container 24 collects inside separator vessel shell 26 and flows down separator vessel drain 22. Separator column 28 is an extension of separator vessel vapor outlet stream 40 extending from the top of separator vessel shell 26 down into liquid container 24. Analyte carrier gas, samples, sample carrier fluid and reagent mix in stripping zone 27 within separator column 28. It is critical that the flow rate of analyte carrier gas into separator vessel 20 be sufficient to ensure that volatilized analytes from one sample are stripped and purged from separator column 28 before succeeding samples are introduced thereto. Gases accumulating inside separator vessel shell 26, but outside separator column 28, are discharged from separator vessel 20 through separator vessel drain 22. Separator column 28 extends from separation vessel vapor outlet stream 40 to well below the liquid level inside liquid container 24. Sample carrier stream 18 and reagent inlet stream 32 flow into separator column 28 within stripping zone 27. Stripping zone 27 is the region within separator column 28 wherein gas bubbles originating from analyte carrier stream 50 flow upwards to the liquid surface. The back pressure in separation vessel vapor outlet stream 40 must be less than the hydrostatic head developed between the liquid surface and the bottom of separator column 28.

Referring again to FIG. 1, reagent is introduced into separator vessel 20 through reagent inlet steam 32 from reagent reservoir 30. Reagent reservoir 30 is an airtight container into which batches of reagent can be added. Additional reservoirs (not shown in FIG. 1) may be used to supply various different reagent to separator vessel 20 depending on the target constituents to be volatilized. For target acid constituents, reagent may consist of, for example, a 10N aqueous solution of sulfuric acid which is used to maintain a pH in separator vessel 20 of less than 2. For analysis of target base constituents, reagent may consist of, for example, a 10N aqueous solution of sodium hydroxide for maintaining the pH of liquid inside separator vessel 20 above 12. Reagent dip tube 33 is an extension of reagent inlet stream 32 extending from the top of reagent reservoir 30 down into the reservoir with an opening near the bottom. During normal operation, the liquid level of reagent in reagent reservoir 30 is maintained above the level of dip tube 33. Flow of reagent into reagent dip tube 33 is achieved by introducing gas propellant from a source not shown through propellant stream 36, which is controlled by propellant pressure indicator and controller 34, into the vapor space contained within reagent reservoir 30. By adding a controlled volume of propellant gas into reagent reservoir 30, a constant flow of reagent into separator vessel 20 is achieved.

Analyte carrier gas is introduced into separator vessel 20 through analyte carrier stream 50 which flows from a source not shown through analyte carrier stream flow indicator 54. The rate of flow of analyte carrier gas is controlled by analyte carrier stream flow controller 52. Nitrogen is but one gas which is suitable as analyte carrier gas.

Volatilized constituents and analyte carrier gas exit from separator vessel 20 through separator vessel vapor outlet stream 40. Separator vessel vapor outlet stream 40 flows through vapor filter 42, then through first detector means 46, then through second detector means 48 and finally to vapor vent 49. Vapor filter 42 removes liquid water from vapor. Such filters are well known and commercially available. One such filter is the Model No. A944-BX, manufactured by Balston Filter Products of Lexington, Mass. First detector means 46 is, for example, a hydrogen sulfide analyzer based on spectrophotometric determinations made in the ultraviolet wavelength region. In this example, first detector means 46 is effective to determine the concentration of volatilized $H_2S$ in separator vessel vapor outlet stream 40. This concentration can be correlated to the concentration of $H_2S$ dissolved in the corresponding liquid sample. First signal line 60 is provided to pass a signal generated by first detector means 46 to processing means, not shown, wherein the concentration of constituents in said liquid stream can be displayed and used, for example, to control a process. Second detector means 48 is, for example, a $CO_2$ analyzer based on spectrophotometric determinations made in the infrared wavelength region. In this example, second detector means 48 is effective to determine the concentration of $CO_2$ vapor in separator vessel vapor outlet stream 40. This concentration can be correlated to the concentration of $CO_2$ dissolved in the corresponding liquid sample. Second signal line 62 is provided to pass a signal generated by second detector means 46 to processing means, not shown, which determines the concentration of constituents in said liquid stream.

The spectrophotometric detectors mentioned hereinabove measure the absorbance of radiation energy by the volatilized constituents. Absorbance is the loss of radiation energy between the radiation source and a detector. The concentration of volatilized constituents is related to absorbance by Beer's Law:

$$A = \log I_o/I = abc$$

where:
A is the absorbance
$I_o$ is the amount of radiation detected absent analytes
I is the amount of radiation detected in the presence of analytes
a is the extinction coefficient of the analyte at a given wavelength
b is the cell pathlength (distance between source and detector), and
c is the concentration of analyte.

For values of A less than about 1.5, the relationship between c and A is linear. It is preferable, therefore, that the cell pathlengths in the detectors 46 and 48 be adjusted so that the product abc over the range of interest of c will result in a value of A within the linear range.

Figure 5:
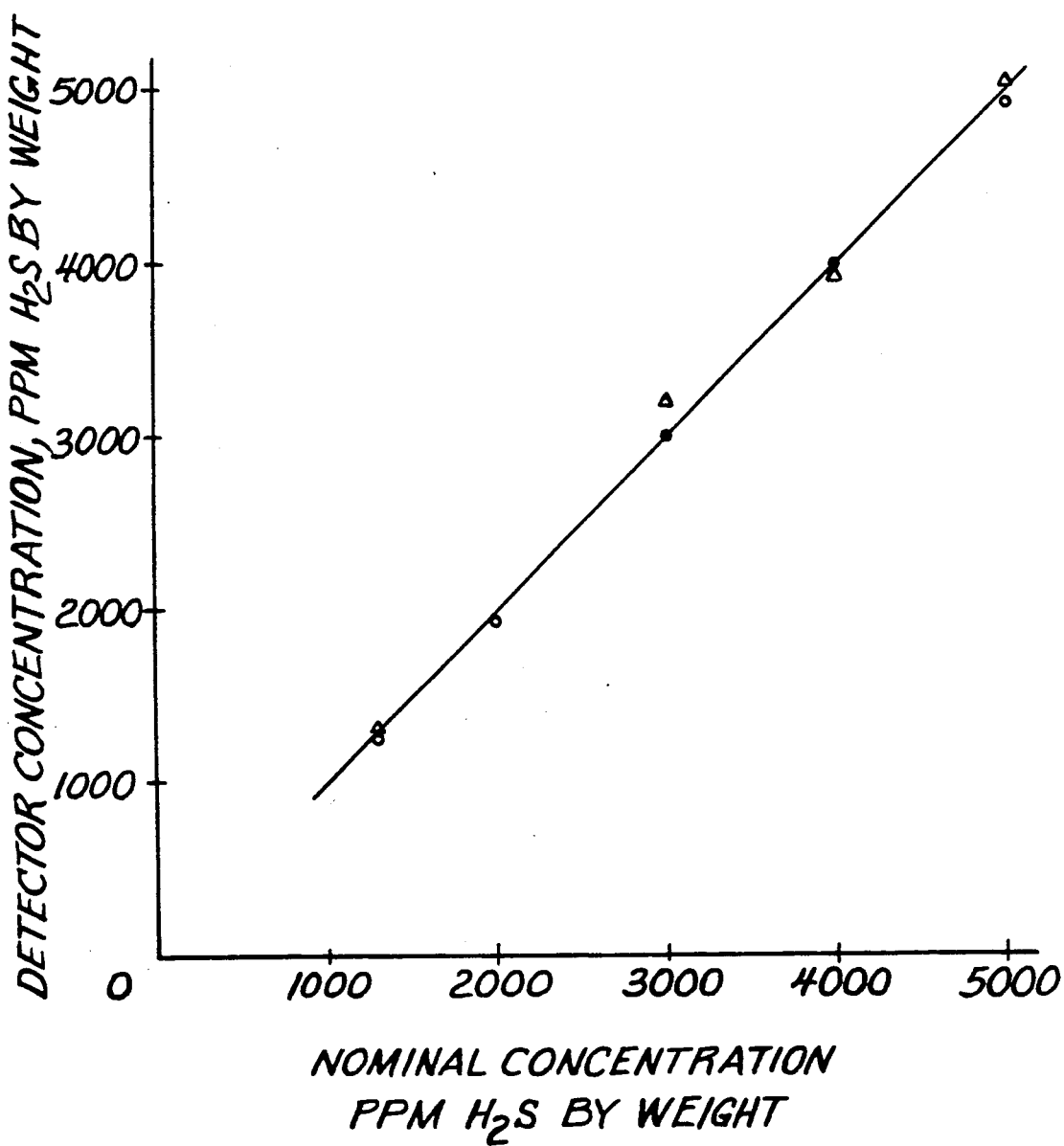
FIG. 5 is a graph showing the nominal concentration of $H_2S$ by weight in a sample versus the detector concentration of $H_2S$ by weight determined using the invention.

Experimental determinations of $H_2S$ concentration made using an apparatus designed in accordance with the invention disclosed herein are presented in FIG. 5. In this case, detector means 46 was used to measure the concentration of $H_2S$ by weight in parts per million (ppm). The nominal ppm of $H_2S$ present in the samples was known and is represented by ppm by weight along the X axis. The samples consisted of $Na_2S$ and $Na_2CO_3$ in a mixture of NaOH and $H_2O$. When the samples are reacted with a strong acid, $H_2S$, $CO_2$ and $NaSO_4$ are produced. Samples containing varying concentrations of $H_2S$ were measured, the determinations being made on different days at room temperature using the same analysis apparatus. Excellent correlation between nominal and detected concentrations of $H_2S$ can be clearly seen in FIG. 5. From this data it can be concluded that using the apparatus described herein accurate, repeatable determinations of the amount of $H_2S$ in the sample can be made.

Figure 6:
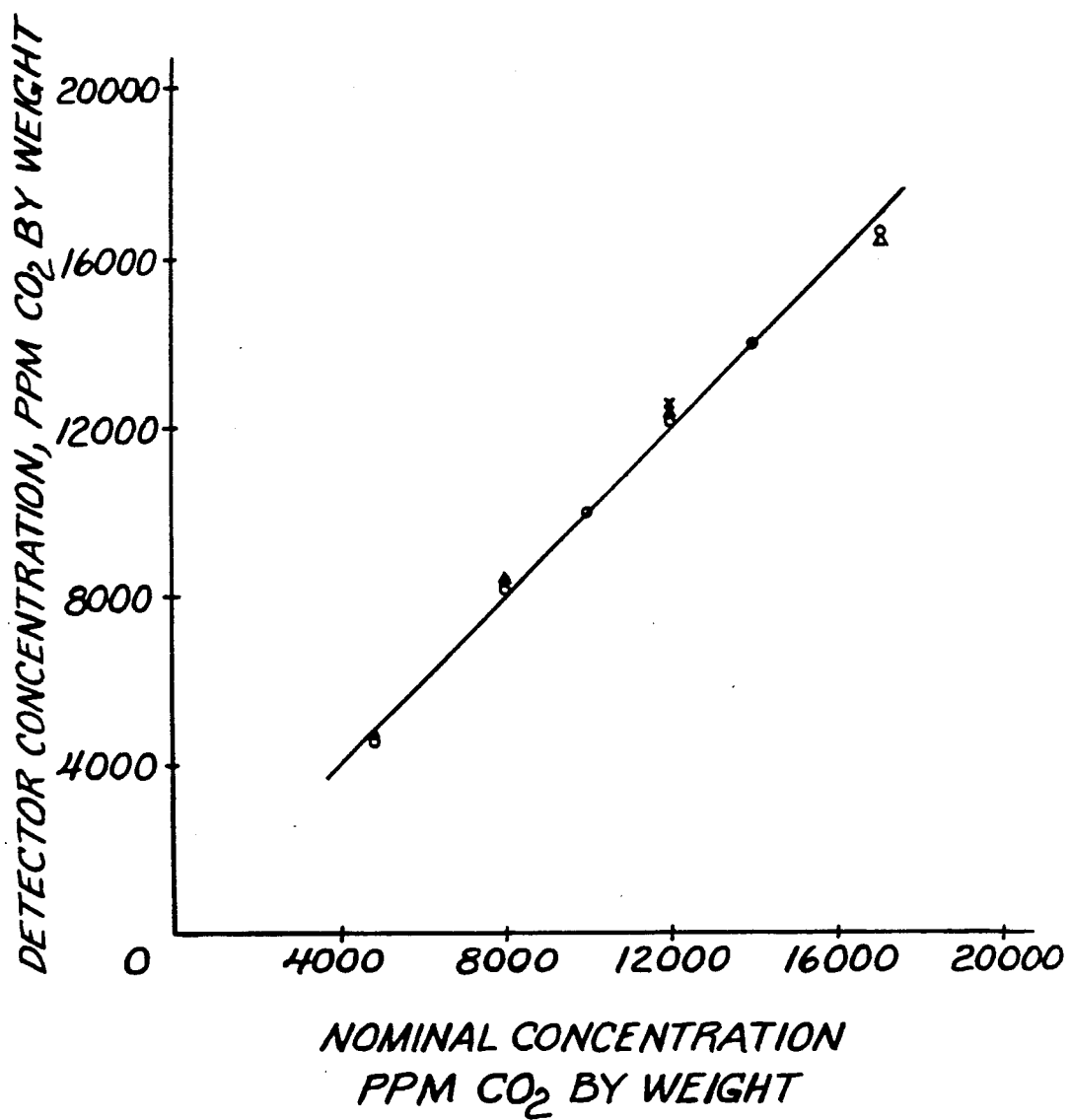
FIG. 6 is a graph showing the nominal concentration of $CO_2$ by weight in a sample versus the detector concentration of $CO_2$ by weight determined using the invention.

Similarly, FIG. 6 represents determinations of $CO_2$ produced when samples consisting of $Na_2S$ and $Na_2CO_3$ in a mixture of NaOH and $H_2O$ were reacted with a strong acid. Samples containing varying concentrations of $CO_2$ were measured, the determinations being made on three separate days at room temperature using the same apparatus. The Y axis represents the detected concentration of $CO_2$ in ppm by weight using detector means 48. The X axis represents the nominal ppm of $CO_2$ by weight. Again, excellent correlation between nominal and detected concentrations of $CO_2$ is demonstrated.

Significant improvements in the control of the amine systems can be achieved using the method and apparatus taught herein. These improvements are attributable to (1) detection of total acid gas concentration rather than just hydrogen sulfide concentration in sour gas, and (2) on-line detection of these constituents that are dissolved in liquid amine streams.

Figure 3:
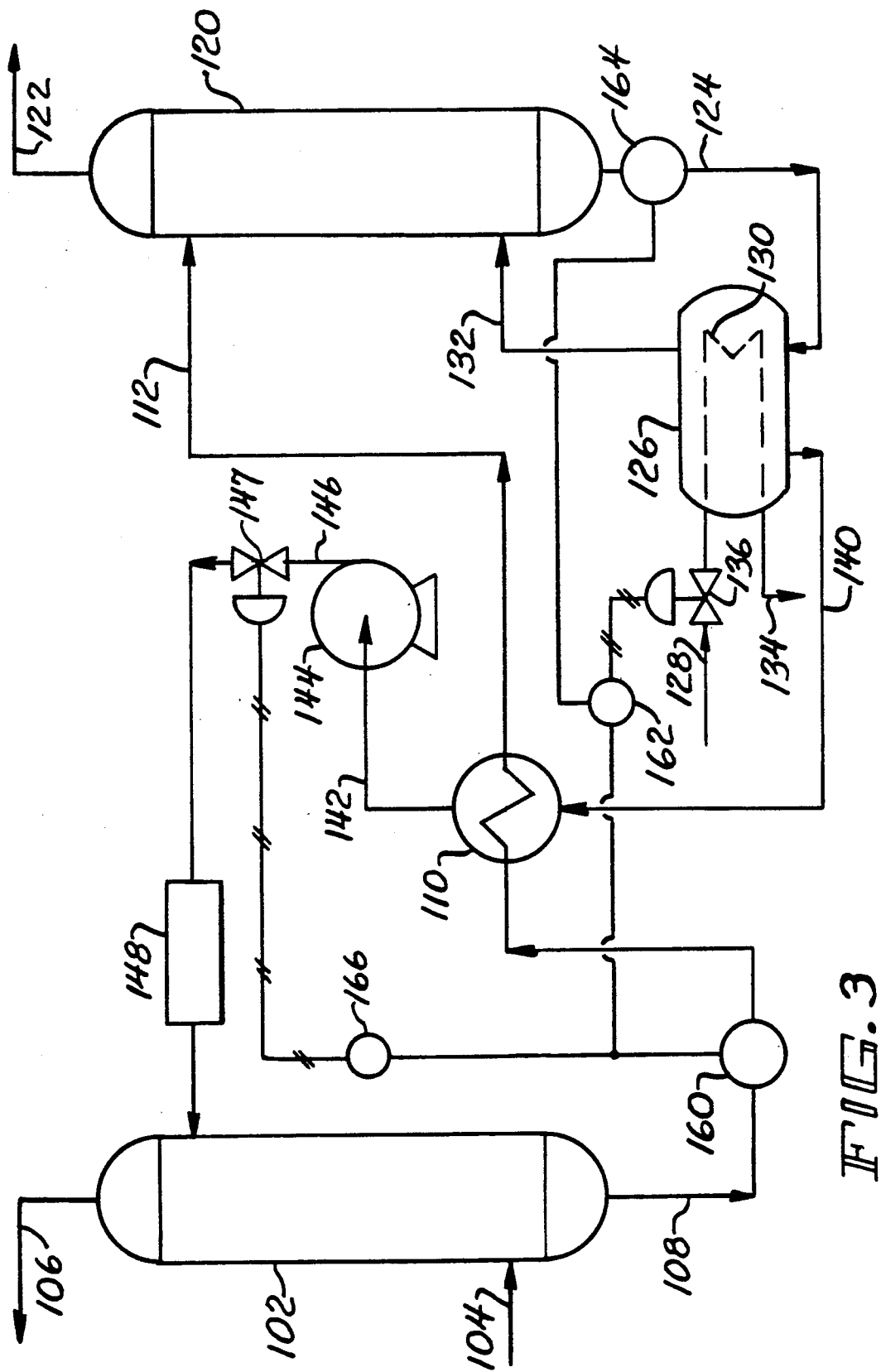
FIG. 3 is a diagram showing a simplified typical amine contactor and regeneration system.

Referring to FIG. 3, the level of $H_2S$ in fuel gas is controlled by the equilibrium established between lean (regenerated) amine entering the top of amine contactor 102 through lean amine pump outlet 146 and sweetened gas exiting amine contactor 102 through sweet gas outlet 106. This equilibrium is a function of the temperature and pressure of amine contactor 102, and the concentration of total acid gas ($H_2S$ and $CO_2$) in the lean amine. High levels of acid gas in the fuel gas entering amine contactor 102 through sour gas inlet 104 must be corrected by lowering the temperature, raising the pressure, lowering the concentration of acid gas in the lean amine, or increasing the flow rate of lean amine to the contactor.

Figure 4:
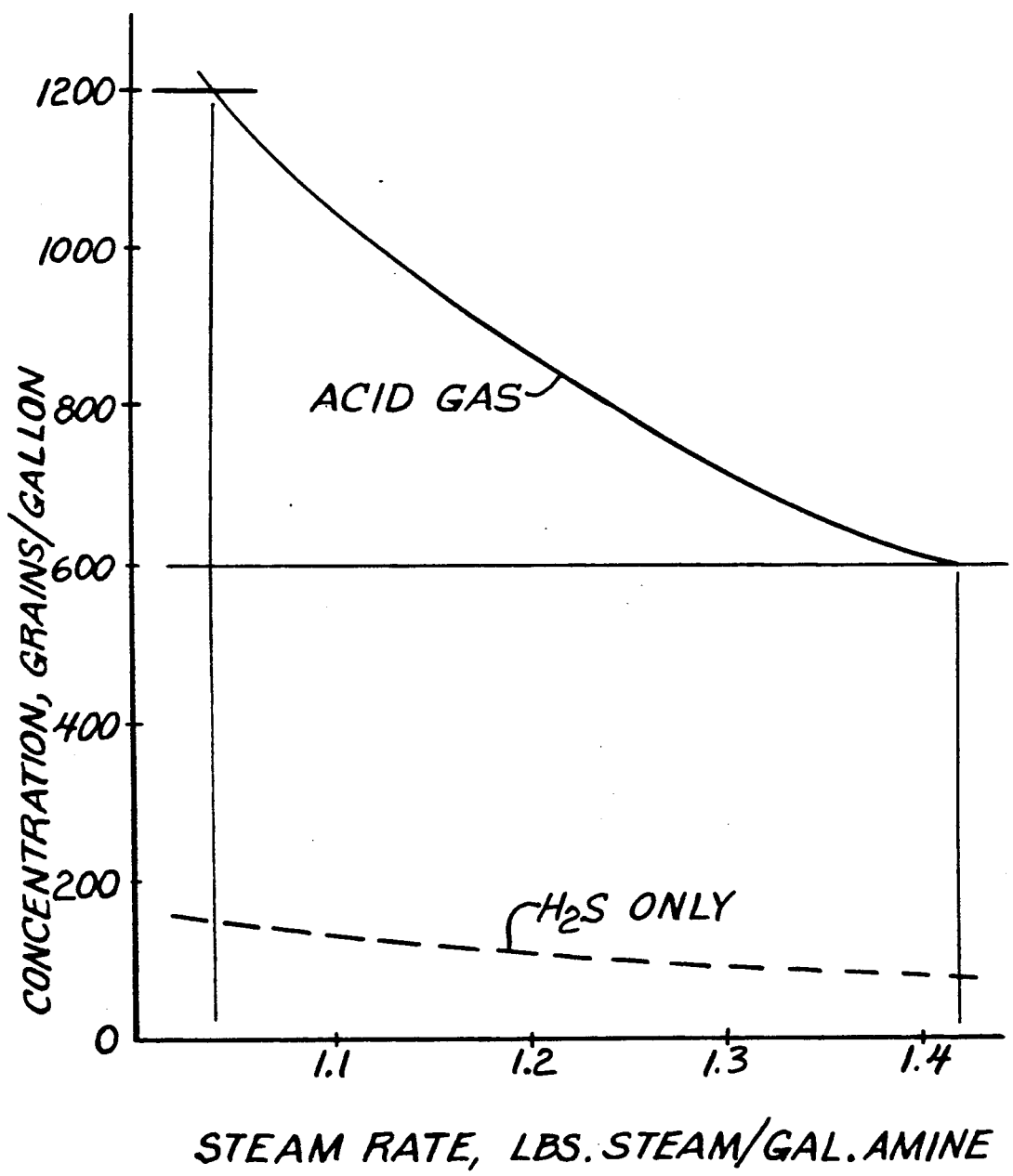
FIG. 4 is a graph showing that hydrogen sulfide represents only a fraction of the total acid gas in lean amine.

It is well known that $H_2S$ represents only a fraction of the total acid gas present in lean amine. However, it is standard in the industry to control amine systems based on analysis for $H_2S$ only, even though total acid gas is a better measure of lean amine quality. Referring to FIG. 4, a comparison is made therein of the steam rate necessary for regenerating rich amine versus (1) the concentration of acid gas, and (2) the concentration of $H_2S$ only in the lean amine. The data in FIG. 4 was acquired during a week-long study of an actual amine unit. In accordance with normal operating procedures, samples of lean amine were obtained and analyzed for $H_2S$ once per 8-hour shift. Stripping steam rates were also noted. For the purpose of the week-long study, total acid gas concentration was also determined. This data shows that within the range of acid gas concentration between 600 and 1,200 grains per gallon, $H_2S$ only represents between 11% and 14% of total acid gas in lean amine. Further, the data shows that $H_2S$ concentration is not proportional to acid gas concentration at different steam rates. Since $CO_2$, which represents most of the remaining acid gas, affects the absorption of $H_2S$ from fuel gas, the importance of controlling regeneration steam rates using determinations of total acid gas in rich amine is clear.

Referring again to FIG. 3, improved steam input control can be achieved by locating an apparatus as disclosed herein, rich amine analyzer 160, in contactor bottoms line 108 and using the signal generated therefrom to control steam flow control valve 136. This is a form of feed forward control whereby information about the quality of rich (contaminated) amine being fed from the bottom of amine contactor 102 through contactor bottoms line 108, first heat exchange means 110, rich amine inlet 112 into amine regenerator 120 is furnished to steam flow controller 162 which in turn controls the flow of steam through steam inlet 128, reboiler steam coil 130 and condensate outlet 134. Reboiler 126 is used to input energy into amine regenerator 120 by heating amine circulated from amine regenerator 120 through reboiler inlet 124, reboiler 126 and back into amine regenerator 120 through reboiler outlet 132. When the level of acid gas concentration in contactor bottoms line 108 exceeds a set point level, steam flow controller 162 adjusts steam flow control valve 136 to increase the flow of steam and hence the energy input into amine regenerator 120. Similarly, when the total acid gas concentration of rich amine in contactor bottoms line 108 falls below a predetermined set point, steam flow controller 162 adjusts steam flow control valve 136 to restrict the flow of steam thereby reducing the amount of energy input into amine regenerator 120.

Heat input into amine regenerator 120 liberates acids absorbed by the amine in amine contactor 102, thereby regenerating amine for recirculation to amine contactor 102. Acid gases are removed from amine regenerator 120 through regenerator overhead line 122. Lean amine exits amine regenerator 120 through lean amine line 140 and first heat exchange means 110. First heat exchange means 110 preheats rich amine and cools lean amine. Lean amine pump 144 is used to return the lean amine to amine contactor 102 through lean amine pump outlet 146 and second heat exchange means 148, which further cools the lean amine.

In addition to improved steam input control into amine regenerator 120 by means of rich amine analyzer 160 due to determination of total acid gas concentration rather than just $H_2S$ concentration, improvements in steam control attributable to on-line responsiveness of rich amine analyzer 160 should also be noted. At present, it is typical for steam input into amine regeneration systems to be based upon $H_2S$ determinations made in quality control laboratories once per operating shift. Clearly, this is less desirable than control based on on-line measurements since quick response to variations in rich amine loading are not possible using the former method.

Control of steam input into reboiler 126 can be further optimized by locating an apparatus as disclosed herein in reboiler inlet line 124 and using the signal generated therefrom to further control steam flow control valve 136. This is a form of feedback control whereby information about the quality of lean amine exiting amine regenerator 120 is furnished to steam flow controller 162 which in turn controls the flow of steam through steam inlet 128, reboiler steam coil 130 and exiting through condensate outlet 134. In this way, steam flow controller 162 is provided information relative to the acid gas content of rich amine being fed to amine regenerator 120 as well as the acid gas concentration in lean amine exiting amine regenerator 120.

Further amine system control enhancement can be achieved by conserving lean amine contacted in amine contactor 102. The flow of lean amine into amine contactor 102 is controlled by lean amine flow controller 166 in connection with lean amine flow control valve 147. By measuring the concentration of acid gas in contactor bottoms line 108 and using this determination to control lean amine flow into amine contactor 102, the rate of addition of lean amine to amine contactor 102 can be maintained in proportion to rich amine loading. More particularly, the rate at which lean amine is supplied to amine contactor 102 can be balanced with the amount of contaminants detected in contactor bottoms line 108 by rich amine analyzer 160. This is important since too much amine input can result in a product penalty in dissolved hydrocarbon. In addition, raw material will be wasted if more amine is degraded than necessary. On the other hand, understripping of amine that is recycled to amine contactor 102 can result in a corrosion problem.

That which is claimed is:

1. A method for on-line determination of the concentration of target constituents in one or more liquid streams containing such constituents comprising:
   essentially continuously and repetitively capturing a plurality of samples of substantially constant size from the liquid stream or streams;
   passing said samples individually to a separation zone wherein succeeding samples are contacted a reagent selected from the group consisting of strong acids and strong bases at separation conditions thereby causing essentially all of the target constituents of each of said succeeding samples to react with said reagent to form volatilized analytes;

separating said volatilized analytes entrained in a liguid within said separation zone by means of an analyte carrier stream which flows at a substantially constant rate through said liquid so as to strip and carry away essentially all of said volatilized analytes of each of said succeeding samples from said liquid; and directing said analyte carrier stream from said separation zone to a detection zone wherein signals are generated which are proportional to the concentration of each target constituent contained in said liquid stream or streams;

determine the concentration of each of said target constituent based upon said signals wherein said target constituents are selected from at least one member of the group consisting of weak acids, weak bases, the soluble salts of weak acids and the soluble salts of weak bases.

2. The method of claim 1 wherein said samples from said liquid stream or streams are passed to said seperation zone by injecting said succeeding samples individually into a separate sample carrier stream which flows from a sample carrier fluid source continuously into said separation zone.

3. The method of claim 2, wherein said sample carrier stream comprises a fluid flowing at an essentially constant rate.

4. The method of claim 3, wherein said sample carrier stream fluid does not substantially chemically react with said samples.

5. The method of claim 3, wherein said sample carrier stream fluid substantially chemically reacts with said samples.

6. The method of claim 3, wherein said sample carrier stream fluid is water.

7. The method of claim 1, wherein said reagent is supplied continuously to said separation zone in a quantity sufficient to volatilize essentially all of the said target constituents of said individual succeeding samples upon contact with said reagent.

8. The method of claim 7, wherein said target constituents are acids and said reagent comprises a strong acid for the determination of the concentration of said target acid constituents.

9. The method of claim 8, wherein said reagent is aqueous sulfuric acid.

10. The method of claim 8, wherein the pH of the liquid within said separation zone is maintained at a level not exceeding 2.

11. The method of claim 8, wherein said target acid constituents are selected from at least one member of the group consisting of hydrogen sulfide and carbon dioxide.

12. The method of claim 7, wherein said target constituents are bases and said reagent comprises a strong base for the determination of the concentration of said of said target base constituents.

13. The method of claim 12, wherein said reagent is aqueous sodium hydroxide.

14. The method of claim 12, wherein the pH of the liquid within said separation zone is maintained at a level not less than 12.

15. The method of claim 12, wherein said target base constituent comprises ammonia.

16. The method of claim 1, wherein said analyte carrier stream comprises a substantially continuously flowing analyte carrier gas which is supplied to said separation zone at essentially a constant flow rate, said analyte carrier gas is used to strip entrained volatilized analyte from said liquid and to carry such stripped volatilized analyte produced by said succeeding samples away from said separation zone to said detection zone.

17. The method of claim 16, wherein said analyte carrier gas is a gas that does not substantially chemically react with the liquid within said separation zone.

18. The method of claim 16, wherein said analyte carrier gas is a gas that substantially chemically reacts with the target constituents within said separation zone to enhance detectability of the constituents.

19. The method of claim 1, wherein said volatilized analytes from said succeeding individual samples pass to one or more detectors within said detection zone, at least one of said detectors constructed so as to measure separately the concentration of each individual target constituent.

20. The method of claim 19, wherein said detectors are spectrophotometric devices for measuring the absorbance of radiation energy by said volatilized analytes.

21. The method of claim 19, wherein said detectors are constructed so as to measure variations in conductivity of liquids of said volatilized analytes.

22. The method of claim 19, wherein said detector or detectors is essentially continuously monitored by:

determining a baseline value for each said detector or detectors in the presence of said analyte carrier gas alone;

repetitively passing volatilized analytes from succeeding individual samples past said detector or detectors by means of an essentially continuously flowing stream of said analyte carrier stream to determine the concentration of said analytes; and verifying substantial identity between said baseline value for each said detector or detectors and the actual value determined by detector after volatilized analytes from one sample have fully passed from said detector or detectors but prior to the introduction to said detector or detectors of the volatilized analytes of succeeding samples.

23. A method for on line determination of the concentration of weak acid constituents in one or more liquid amine streams in a gas sweetsning process comprising:

essentially continuously and repetitively capturing a plurality of samples of substantially constant size from the liquid amine stream or streams;

passing said samples individually to a separation zone wherein succeeding samples are contacted with a reagent comprising a strong acid at separation conditions thereby causing essentially all of the weak acid constituents of each of succeeding said samples to react with said reagent to form volatilized analytes;

separating said volatilized analytes entrained in a liquid within said separation zone with an analyte carrier stream which flows at a substantially constant rate through said liquid so as to strip and carry away essentially all of the weak acid constituents of each of said succeeding samples from said liquid; and directing said analyte carrier stream from said separation zone to a detection zone wherein signals are generated which are proportional to the concentration of each weak acid constituent contained in said liquid amine stream or streams;

determine the concentration of each weak acid constituents based on said signals wherein said weak acid constituents are selected from at least one member of the group consisting of hydrogen sulfide, carbon dioxide, the soluble salts of hydrogen sulfide and the soluble salts of carbon dioxide.

24. The method of claim 23, wherein said samples from said liquid amine stream or streams are passed to said separation zone by injecting said succeeding samples individually into a separate carrier stream comprising a fluid that flows at a constant rate from a sample carrier fluid source into said separation zone.

25. The method of claim 24, wherein said sample carrier stream fluid is water.

26. The method of claim 23, wherein said reagent comprises a strong acid which is supplied continuously to said separation zone at a rate and strength which upon contact will volatize essentially all of said weak acid constituents of each of said succeeding samples.

27. A method for on line determination of the concentration of ammonia in one or more water influent streams in a waste water process comprising:

essentially continuously and repetitively capturing a plurality of samples of substantially constant size from said water influent stream or streams;

passing said samples individually to a separation zone wherein succeeding samples are contacted with a reagent at separation conditions thereby causing essentially all of the ammonia of each of said succeeding samples to react with said reagent to form volatilized analytes;

separating said volatilized analytes entrained in a liquid within said separation zone with an analyte carrier stream which flows at a substantially constant rate through said liquid so as to strip and carry away essentially all of the ammonia of each of said succeeding samples from said liquid; and directing said analyte carrier stream from said separation zone to a detection zone wherein signals are generated which are proportional to the concentration of ammonia contained in said water influent stream or streams; determine the concentration of ammonia based upon said signal.

28. The method of claim 27, wherein said samples from said water influent stream or streams are passed to said separation zone by individually injecting said succeeding samples into a separate sample carrier stream comprising a fluid that flows at a constant rate from a source into said separation zone.

29. The method of claim 28, wherein said sample carrier stream fluid is water.

30. The method of claim 28, wherein said reagent comprises a strong base which is supplied continuously to said separation zone at a rate and strength which upon contact will volatilize essentially all of said weak base constituents of each of said succeeding samples.

31. A method for on-line determination of the concentration of target constituents in one or more liquid streams containing such constituents comprising:

essentially continuously and repetitively capturing a plurality of samples of substantially constant size from the liquid stream or streams;

passing said samples individually to a separation zone wherein succeeding samples are contacted with a reagent at separation conditions thereby causing essentially all of the target constituents of each of said succeeding samples to react with said reagent to form volatilized analytes;

separating said volatilized analytes entrained in a liquid within said separation zone with an analyte carrier stream which flows at a substantially constant rate through said liquid so as to strip and carry away essentially all of said volatilized analytes of each of said succeeding samples from said liquid wherein said analyte carrier stream comprises a substantially continuously flowing analyte carrier gas which is supplied to said separation zone at essentially a constant flow rate, said analyte carrier gas is used to strip entrained volatilized analyte from said liquid and to carry said stripped volatilized analyte produced by said succeeding samples away from said separation zone and wherein said analyte carrier gas substantially chemically reacts with said target constituents within said separation zone to enhance detectability of said constituents; and directing said analyte carrier stream from said separation zone to a detection zone wherein signals are generated which are proportional to the concentration of each target constituent contained in said liquid stream or streams; determine the concentration of ammonia based upon said signals wherein said target constituents are selected from at least one member of the group consisting of weak acids, weak bases, the soluble salts of weak acids and the soluble salts of weak bases.

* * * * *